(12) United States Patent
Kovarik et al.

(10) Patent No.: US 8,023,722 B1
(45) Date of Patent: Sep. 20, 2011

(54) RADIOGRAPHY TEST SYSTEM AND METHOD

(75) Inventors: James J. Kovarik, Bartlett, IL (US); Brent D. Burns, Elgin, IL (US); Kevin J. Umess, Saint Charles, IL (US)

(73) Assignee: Lixi, Inc., Huntley, IL (US)

(*) Notice: Subject to any disclaimer, the term of this patent is extended or adjusted under 35 U.S.C. 154(b) by 0 days.

(21) Appl. No.: 12/928,765

(22) Filed: Dec. 17, 2010

Related U.S. Application Data

(63) Continuation of application No. 11/701,183, filed on Feb. 1, 2007, now Pat. No. 7,912,273.

(51) Int. Cl.
*G06K 9/00* (2006.01)

(52) U.S. Cl. ....................................................... 382/141

(58) Field of Classification Search .................. 382/132, 382/141–152; 378/98
See application file for complete search history.

(56) References Cited

U.S. PATENT DOCUMENTS

| | | |
|---|---|---|
| 3,178,576 A | 4/1965 | Arvanetakis |
| 4,289,030 A | 9/1981 | Alers et al. |
| 4,587,555 A | 5/1986 | Carollo et al. |
| 4,604,649 A | 8/1986 | Carollo et al. |
| 5,192,491 A | 3/1993 | Schulz |
| 5,362,962 A | 11/1994 | Barborak et al. |
| 5,526,691 A | 6/1996 | Latimer et al. |
| 5,714,688 A | 2/1998 | Buttram et al. |
| 6,157,699 A | 12/2000 | Dunn |
| 6,392,421 B1 | 5/2002 | Amini |
| 6,647,801 B1 | 11/2003 | Deuar |
| 7,719,266 B1 | 5/2010 | Zamanzadeh et al. |
| 7,773,725 B2 | 8/2010 | Gordon, III et al. |
| 7,826,088 B2 | 11/2010 | Silverbrook |
| 7,912,273 B2 | 3/2011 | Survant et al. |
| 2004/0189289 A1 | 9/2004 | Atherton |
| 2009/0199642 A1 | 8/2009 | Fukutomi et al. |
| 2009/0301202 A1 | 12/2009 | Bisiaux et al. |
| 2010/0017137 A1 | 1/2010 | Legendre et al. |
| 2010/0052670 A1 | 3/2010 | Kwun et al. |
| 2010/0106431 A1 | 4/2010 | Baba et al. |
| 2010/0107767 A1 | 5/2010 | Kane et al. |
| 2010/0199767 A1 | 8/2010 | Ganin |
| 2010/0207620 A1 | 8/2010 | Gies |
| 2010/0236330 A1 | 9/2010 | Nyholt et al. |
| 2010/0278373 A1 | 11/2010 | Capron et al. |

FOREIGN PATENT DOCUMENTS

| | | |
|---|---|---|
| JP | 62008089 | 1/1987 |
| JP | 4048205 | 2/1992 |
| JP | 2001004562 | 1/2001 |

OTHER PUBLICATIONS

Twomey, "Inspection Techniques for Detecting Corrosion Under Insulation", Feb. 1998, vol. 3, No. 2, pp. 1-5.

*Primary Examiner* — Daniel Mariam
(74) *Attorney, Agent, or Firm* — Sheridan Ross P.C.

(57) ABSTRACT

A system and method for monitoring degradation of a device having a metal layer and a composite layer, such as a vehicle-mounted boom arm. The system can include a collar mounted on an outer surface of the device, a radiography device movably coupled to the collar, and a monitor. The radiography device can include a source of radiography signals positioned to direct radiography signals through at least a portion of the device and a detector to detect radiography signals that have passed through the device. The monitor can be connected to the detector to display an image of the device generated from the detected radiography signals. Anomalies in the device image can represent degradation in the device.

9 Claims, 3 Drawing Sheets

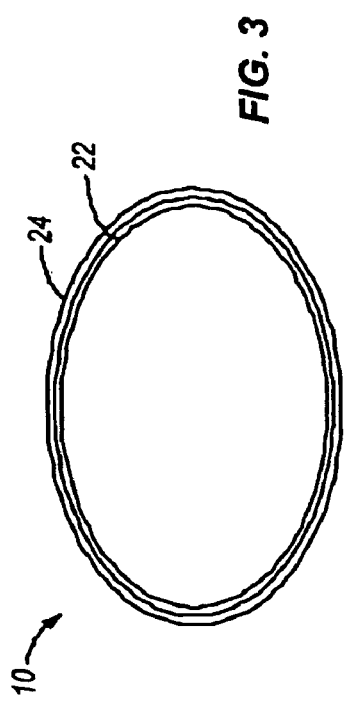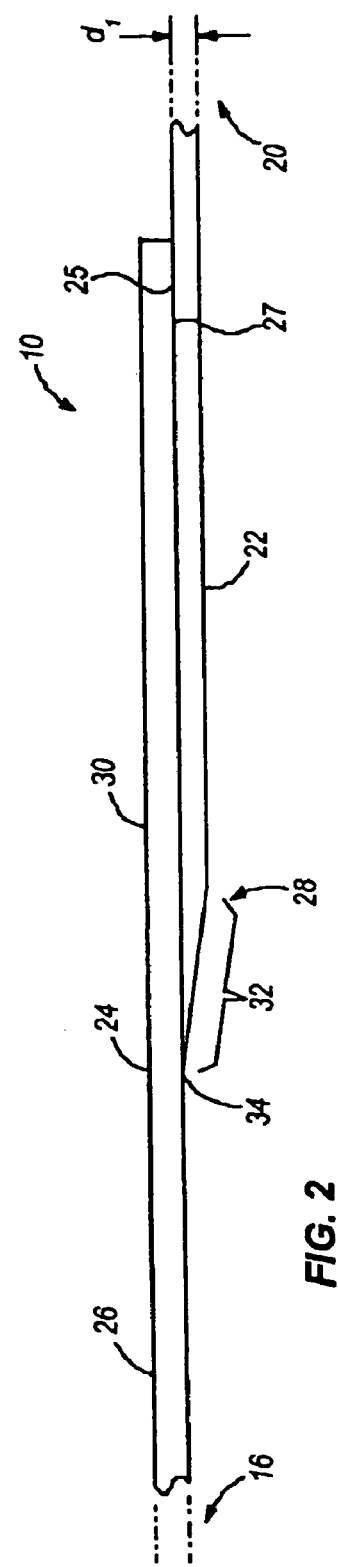

RADIOGRAPHY TEST SYSTEM AND METHOD

RELATED APPLICATIONS

The present application is a continuation-in-part of U.S. Ser. No. 11/701,183 filed Feb. 1, 2007 entitled "Radiography Test System and Method," the entirety of which is incorporated herein by this reference.

FIELD OF THE INVENTION

The invention relates to a system and method for non-destructive examination of degradation, such as corrosion and wear, on a non-visible interior of a device having a metal layer bonded to a composite layer, such as a vehicle-mounted boom arm.

BACKGROUND

Telephone and utility service providers frequently inspect or repair lines, trees, and other objects located at elevated heights. Boom arms fitted with baskets are commonly mounted to vehicles for elevating personnel carried within the basket. Boom arms for such vehicles can be constructed in a variety of configurations, including, for example, an over-center boom arm that can unfold from a horizontal position to a vertical position.

Boom arms are typically hollow tubes that are strong and lightweight with a multi-layer construction. One type of boom arm has an inner metal layer bonded to an intermediate composite layer (e.g., a steel portion that extends 10 to 14 inches across a connection point between fiberglass portions). An outer layer is constructed of a protective material, such as a gel-coat, and is bonded or applied over the composite layer.

The metal layer and the composite layer have different stiffnesses. To provide a smooth transfer of bending stresses created by the load in the basket from the composite layer to the metal layer, the end of the metal layer is tapered over a region around the inner circumference of the boom arm. The tapered region allows a band of stress between the metal layer and the composite layer to dissipate. For example, the tapered region diffuses the stress into a band having a width of about six to ten inches. Without the tapered region, the stress would form a stress line, increasing the likelihood of failure of the composite layer.

The metal layer, and particularly the tapered region of the metal layer, is subject to degradation by, for example, corrosion or wear. When corrosion occurs, rust is produced and the thickness of the metal material at the tapered region is reduced. Because the production of rust does not occur uniformly, the remaining material at the tapered region forms into peaks and valleys, increasing the magnitude of stresses at stress points, rather than across a band. Rust is also worn into the composite layer adjacent to corrosion spots in the metal layer, eroding the composite material and reducing the strength of the composite layer. Finally, as metal and composite material at the tapered region is depleted by degradation, gaps form between the composite layer and the metal layer, reducing the generally uniform transfer of stresses at the tapered region.

Each vehicle-mounted boom arm can be subject to different environmental conditions depending on the use of the boom arm and the local climate. As a result, it is difficult to predict if and when degradation such as corrosion and wear will occur. Furthermore, because degradation occurs on the inside of the boom arm, there may not be any indicators of corrosion, erosion, wear etc. on the exterior or visible surface of the boom arm. In order to access the interior of the boom arm for examination, the boom arm would have to be disassembled or even destroyed with certain boom configurations.

SUMMARY

Accordingly, a need exists for a system and method of examining degradation, such as corrosion and wear, present on a non-visible interior of a device having a metal layer and a composite layer, such as a vehicle-mounted boom arm, without having to destroy or disassemble the device.

In one embodiment, the invention provides a method for non-destructively examining degradation on an interior of a device having a metal layer and a composite layer. Radiography signals are directed through a region of interest of the device, which includes the metal layer and the composite layer. Radiography signals that have passed through the device are detected. An image of the metal layer and the composite layer at the region of interest is generated from the detected radiography signals. Anomalies in the device image representing degradation in the region of interest are identified.

In another embodiment, the invention provides a system for non-destructively examining degradation on an interior of device having a metal layer and a composite layer. The system includes a collar sized and shaped to be mounted on an outer surface of the device, a radiography device movably coupled to the collar, and a monitor. The radiography device includes a source of radiography signals arranged to direct radiography signals through at least a portion of the metal layer and the composite layer and a detector for detecting the radiography signals. The monitor is connected to the detector to display an image of the device generated from the detected radiography signals.

In yet another embodiment, the invention provides a method for monitoring degradation on an interior of a device having a metal layer and a composite layer. A region of interest on an interior of the device is non-destructively examined for degradation, and the degradation is quantified. The device is placed in a first monitoring schedule if substantially no degradation is present on the device. The device is removed from service if a quantity of degradation in excess of a degradation threshold is present on the device. The device is placed in a second monitoring schedule if a quantity of degradation less than the degradation threshold is present on the device.

Other aspects of the invention will become apparent by consideration of the detailed description and accompanying drawings.

BRIEF DESCRIPTION OF THE DRAWINGS

FIG. 2 is a longitudinal cross-sectional view of a portion of a boom arm.

FIG. 3 is a lateral cross-sectional view of the boom arm of FIG. 2.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings, and can include electrical connections or couplings, whether direct or indirect.

Figure 1:
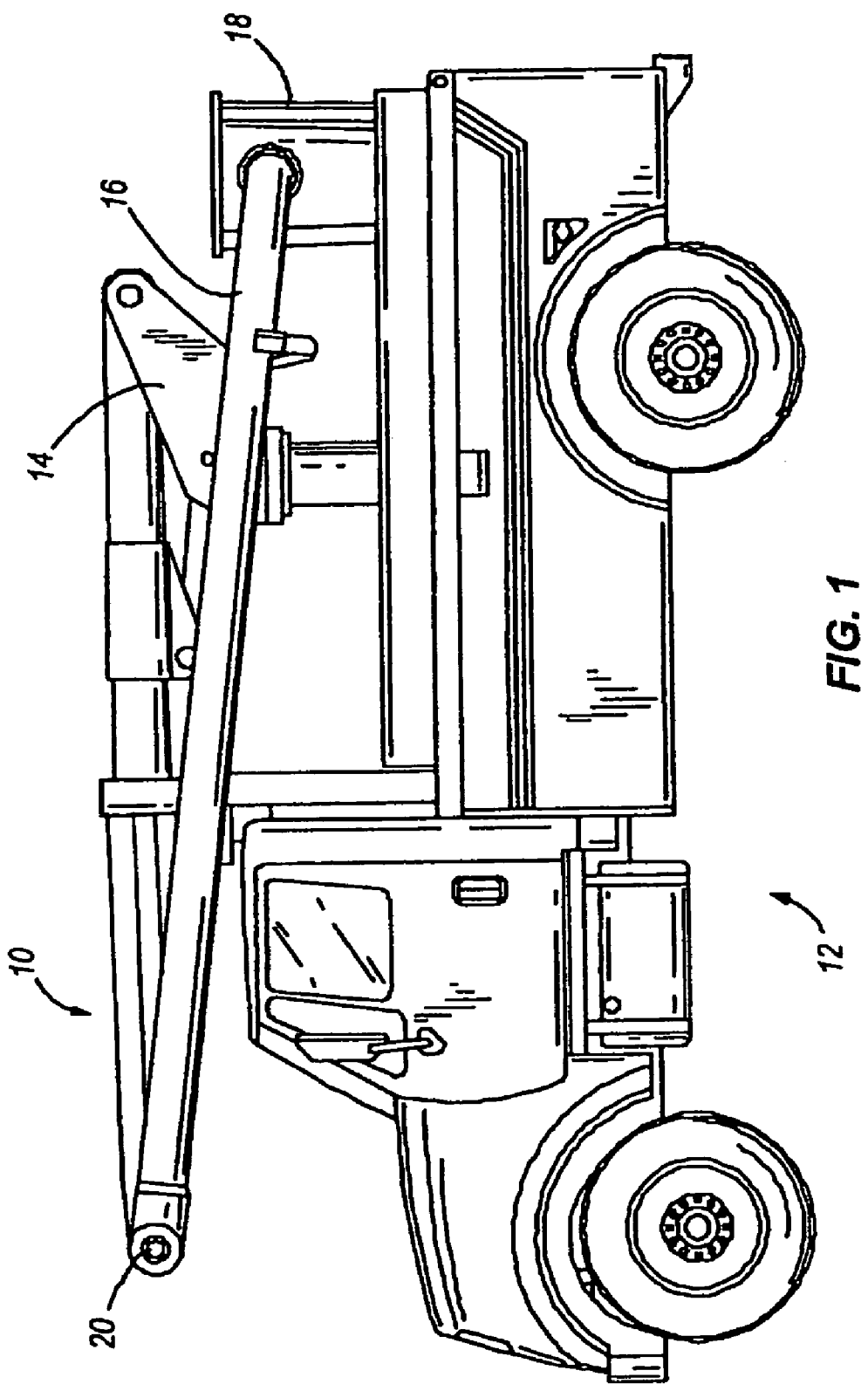
FIG. 1 is a side view of a motorized vehicle with a boom arm in a folded configuration.

FIG. 1 illustrates a boom arm 10 mounted to a motorized vehicle 12 of the type commonly used to access elevated objects, such as power lines and trees. A first end 14 of the boom arm 10 is mounted to the vehicle 12, while a second end 16 of the boom arm 12 is coupled to a passenger basket 18. The boom arm 10 can include an elbow joint 20 so that the boom arm 10 can be stored folded into a horizontal or lengthwise configuration while not in use, as shown in FIG. 1. The boom arm 10 can be unfolded into a vertical position with the basket 18 elevated while in use.

FIGS. 2 and 3 illustrate the construction of the boom arm 10, which is a multi-layer hollow, tubular member. This type of multi-layer construction may also be present in other types of devices or equipment, such as wire spreaders, cranes, platform lifts, cable placers, etc. In the electric utility industry specifically, composite materials are used primarily for construction in order to provide insulation from the electric line voltages. Metals are generally only used to reinforce the joints between composite structures. However, failure occurs at these metal-reinforced joints between composite structures. As shown in FIGS. 2 and 3 for a vehicle-mounted boom arm 10, an inner layer 22 of the boom arm 10 is generally formed of a metal, such as steel. An intermediate layer 24 of the boom arm 10 is generally formed of a composite material, such as fiberglass. An inner surface 25 of the composite layer 24 is bonded to an outer surface 27 of the metal layer 22 to secure the layers to one another. A tapered or transition region 32 is formed at an end 28 of the metal layer 22, where the metal layer 22 is tapered from a first thickness $d_1$ to a pointed or almost pointed edge 34 extending around the circumference of the metal layer 22. However, the transition region 32 may not be tapered in some boom arms. The composite layer 24 is generally longer than the metal layer 22, so that an end 26 of the composite layer 24 forms a tube extending beyond the end 28 of the metal layer 22. As shown in FIG. 5, an outer layer 36, such as a gel coat, of the boom arm 10 can be a protective coating formed or bonded to the intermediate layer 24.

Figure 4:
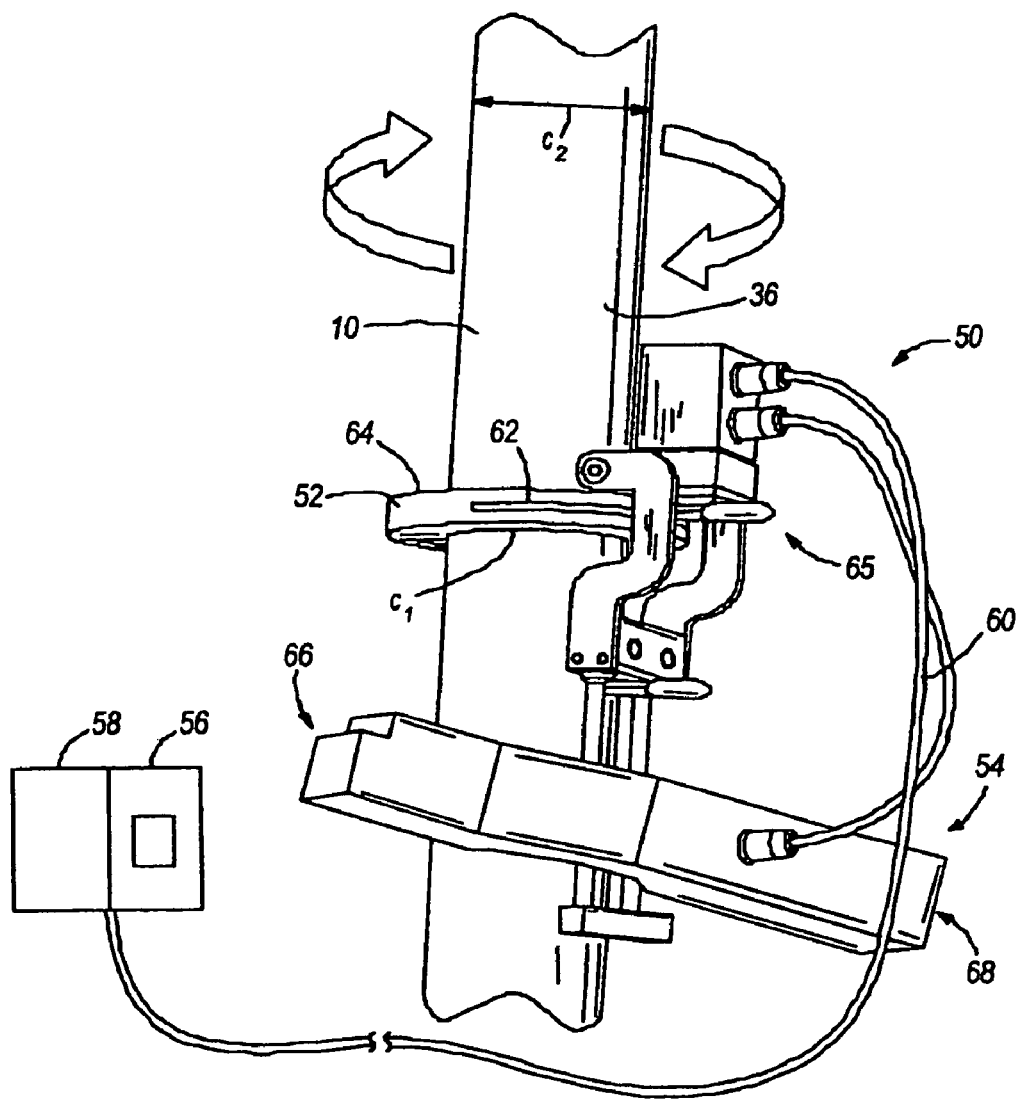
FIG. 4 is a perspective view of a radiography degradation detection system according to one embodiment of the invention mounted to a boom arm.

FIG. 4 illustrates a radiography degradation detection system 50 according to one embodiment of the invention mounted to boom arm 10. The detection system 50 can include a collar 52, a radiography device 54 coupled to the collar 52, and a monitor 56 connected to the radiography device 54.

The collar 52 can be a ring-like member sized and shaped for mounting to an outside of the boom arm 10. An inner circumference $c_1$ of the collar 52 can be slightly greater than an outer circumference $c_2$ of the boom arm 10. The collar 52 can include a hinge or other mechanism to facilitate at least partially opening and mounting the collar 52 to the boom arm 10. The collar 52 can include a securing mechanism 62 to secure the collar 52 to the boom arm 10. The securing mechanism 62 can be a clamp, a compression collar, a magnet, bolts, etc.

In some embodiments, the collar 52 can include a track 64 along which the radiography device 54 can move. The radiography device 54 can be coupled to the collar 52 and can be moved around the circumference of the boom arm 10 by moving along the track 64. The radiography device 54 can include a movement mechanism 65, such as a motor, for coupling the radiography device 54 to the collar 52 and for moving the radiography device 54 along the track 64. In one embodiment, the radiography device 54 can be moved about 360 degrees along the track 64 in order to move around substantially the entire circumference of the boom arm 10. In another embodiment, the radiography device 54 can be moved about 180 degrees along the track 64 or about half of the boom arm circumference.

As shown in FIG. 4, the radiography device 54 includes a source 66 of radiography signals 67 and a detector 68 for detecting radiography signals. In one embodiment, the radiography signals 67 are X-ray signals. The source 66 of radiography signals 67 and the detector 68 can be spaced apart on the collar 52 and can be positioned so that radiography signals 67 from the source 66 are directed into the boom arm 10 through both the metal layer 22 and the composite layer 24 toward the detector 68. The detector 68 can be positioned to detect radiography signals 67 which have passed through the boom arm 10. The degradation detection system 50 can be mounted to the boom arm 10 so that the radiography signals 67 pass through a region of interest of the boom arm 10, such as the tapered region 32.

As shown in FIG. 4, the monitor 56 can generate and display an image of the interior of the boom arm 10 from the radiography signals detected by the detector 68. The monitor 56 can be a handheld device, a personal computer, a laptop, or another suitable electronic device and can include a screen for displaying the image and/or data obtained from the detected radiography signals. The detected radiography signals can be displayed as still images or can be displayed as a moving image as the radiography device 54 travels around the boom arm 10 along the track 64. The monitor 56 can display substantially all or a portion of the circumference of the boom arm 10 at a given time. In one embodiment, the monitor 56 displays approximately an 11 degree arc of the boom arm 10 circumference at a given time. The degradation detection system 50 can include a control mechanism 58 that controls movement of the radiography device 54, as well as overall operation of the degradation detection system 50. The degradation detection system 50 can further include cables and connectors 60 for connecting the radiography device 54 to the monitor 56 and/or to other components of the degradation detection system 50. The cables and connectors 60 can be replaced with a wireless connection.

In one embodiment, visual analysis of the image of the boom arm 10 on the monitor 56 is used to identify and/or quantify degradation of the boom arm 10. This analysis can be performed manually by the operator of the degradation detection system 50 upon viewing the image on the monitor 56. In other embodiments, a software program, image analysis tool, or other computerized device can be used to automatically analyze the image of the boom arm 10 to identify and/or quantify degradation. In still other embodiments, a software program, signal analysis tool, or other computerized device can be used to analyze not the image, but the detected radiography signals themselves, in order to identify and/or quantify degradation. Such computerized devices can be installed on a handheld device, laptop, or personal computer that is connected to the monitor 56 and/or the radiography device 54, or can be integrated into the monitor 56. The results of the analysis by the computerized device can be displayed on the monitor 56 or another suitable display device. In addition, such data can be archived, uploaded to a database, transmitted to another party, etc. Finally, in some embodiments, even though identification and quantification of degradation can be carried out automatically by a computerized device, the images of the boom arm 10 can also be displayed on the monitor 56 for visual review by the operator of the degradation detection system 50.

Incorporated herein by this reference are various patents and patent publications that one of skill in the art will appreciate can be used in conjunction with the teaching and guidance provided herein to perform particular operations on various devices and in varying conditions. For the purposes of brevity while still complying with written description and enablement requirements, the following are hereby incorporated herein by this reference in their entireties: U.S. Pat. Nos. 6,647,801; 7,719,266; 7,719,266; 7,773,725; 7,826,088; 6,392,421; 20090199642; 20090301202; 20100017137; 20100052670; 20100106431; 20100107767; 20100199767; 20100207620; 20100236330; 20100278373

In some embodiments, the first detector may include a "bucket detector." A bucket detector refers to a multimode detector where all the modes propagating through an object are measured jointly. The bucket detector detects the presence, but not the location, of a photon. A bucket detector collects all the photons scattered by the object and acts like a time gate for a second detector. A time gate allows the second detector to know when to begin its observation and start counting coincidences.

In certain embodiments, a detector assembly and monitor which produces a real-time visible image may be supplanted with a detector employing a measurement device and display which produces a real-time display depicting density or material detected. In other embodiments, in addition to movement of the system about either the collar or around the device (e.g. boom), the detector assembly is moved along an axis parallel to the centerline of the device (e.g. boom). Real-time images on monitors of degradation or corrosion between a composite layer and metal layer (insulated piping) using a tangential scanning technique can be accomplished by having at least two collars and at least two separate monitors provided. Also included in various embodiments are attachment mechanisms that permit the variation of orientations to provide desired visibility around or about a particular device, such as a boom. For example, a tipping detector assembly may be employed to provide visibility to degradation artifacts not visible in 'perpendicular' tangent orientation—thus permitting angular adjustability to improve inspections. Still other embodiments comprise, in addition to producing images or measuring at location at the boundary of a metal layer and composite layer, the ability to move the system along an arc in a plane perpendicular to the centerline axis of the device (e.g. boom/pipe) while simultaneously allowing for movement along a collar associated with or around the device. More than one imaging device can be employed to achieve desired detection, such that in addition to an x-ray tube, other types of diction systems can be employed, such as an alternate energy source, e.g. a gamma energy emitting radioactive isotope. Yet other embodiments involve the use of an X-ray tube (source) and detector/measurement assembly that is not mounted to a common platform and that is not fixed in position with respect to each other. In certain embodiments a color is not employed at all, but rather is replaced with an external measurement system that determines the position of the source and the position of the detector and computes their position with respect to the other.

Thus, the invention provides, among other things, a system and method for non-destructive examination of degradation on an interior of a boom arm. Various features and advantages of the invention are set forth in the following claims.

The invention claimed is:

1. A system for non-destructively examining degradation on an interior of a device having a metal layer and a composite layer, the system comprising:
   a collar sized and shaped to be mounted on an outer surface of the device;
   a radiography device movably coupled to the collar, the radiography device including a source of radiography signals positioned to direct radiography signals through at least a portion of the metal layer and the composite layer and a detector to detect the radiography signals; and
   a monitor connected to the detector to display an image of the device generated from the detected radiography signals.

2. The system as set forth in claim 1, wherein the collar is a ring-like member sized and shaped for mounting to an outside of a boom arm.

3. The system as set forth in claim 2, wherein the collar has an inner circumference is slightly greater than an outer circumference of the boom arm.

4. The system as set forth in claim 2, wherein the collar includes a hinge to facilitate at least partially opening and mounting the collar to the boom arm.

5. The system as set forth in claim 2, wherein the collar includes a securing mechanism to secure the collar to the boom arm, said securing mechanism selected from the group consisting of a clamp, a compression collar, a magnet, and a bolt.

6. The system as set forth in claim 2, wherein the radiography device is coupled to the collar in a manner so that it is movable around the circumference of the boom arm.

7. The system as set forth in claim 2, wherein the radiography device is movable about 360 degrees along the track in order to move around substantially the entire circumference of the boom arm.

8. The system as set forth in claim 2, wherein a source of radiography signals and a detector are spaced apart on the collar.

9. The system as set forth in claim 1, wherein the collar includes a track along which the radiography device can move.

* * * * *